(12) United States Patent
Gailloud et al.

(10) Patent No.: US 8,771,309 B2
(45) Date of Patent: *Jul. 8, 2014

(54) METHODS AND APPARATUS FOR RAPID ENDOVASCULAR VESSEL OCCLUSION AND BLOOD FLOW INTERRUPTION

(71) Applicant: ArtVentive Medical Group, Inc., San Marcos, CA (US)

(72) Inventors: Philippe Gailloud, Baltimore, MD (US); Leon Rudakov, San Marcos, CA (US)

(73) Assignee: ArtVentive Medical Group, Inc., San Marcos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/670,345

(22) Filed: Nov. 6, 2012

(65) Prior Publication Data

US 2013/0053879 A1 Feb. 28, 2013

Related U.S. Application Data

(63) Continuation of application No. 11/825,956, filed on Jul. 9, 2007, now Pat. No. 8,328,840.

(51) Int. Cl.
*A61M 29/00* (2006.01)
*A61B 17/12* (2006.01)

(52) U.S. Cl.
CPC ..... *A61B 17/12172* (2013.01); *A61B 17/12031* (2013.01); *A61B 17/12036* (2013.01); *A61B 2017/1205* (2013.01); *A61B 17/12109* (2013.01)
USPC ........................................................ 606/191

(58) Field of Classification Search
CPC ........................................... A61B 2017/12022

USPC .............. 623/1.11, 1.12, 1.24, 1.25; 606/108, 606/200; 128/831, 843
See application file for complete search history.

(56) References Cited

U.S. PATENT DOCUMENTS

| 4,705,517 A | 11/1987 | DiPisa, Jr. |
| 4,733,665 A | 3/1988 | Palmaz |
| 4,739,762 A | 4/1988 | Palmaz |
| 4,776,337 A | 10/1988 | Palmaz |

(Continued)

FOREIGN PATENT DOCUMENTS

| WO | WO 9912484 | 3/1999 |
| WO | WO 2006/034153 | 3/2006 |

OTHER PUBLICATIONS

Serbinenko, F.A., Balloon Catheterization and Occlusion of Major Cerebral Vessels, J. Neurosurg. Aug. 1974, pp. 125-145, vol. 41.

(Continued)

*Primary Examiner* — Darwin Erezo
*Assistant Examiner* — Jonathan Hollm
(74) *Attorney, Agent, or Firm* — James W. Hill; Nathan S. Smith; McDermott Will Emery & LLP

(57) ABSTRACT

An occluding device including expandable scaffold and a flow-limiting member is described. In some embodiments the scaffold is an expandable or self-expanding stent deliverable over a guide wire. The flow-limiting member can include a valve that can be closed following deployment. On deployment the stent and flow-limiting member can engage an inner surface of a body cavity lumen, blocking flow of material. In some embodiments the body cavity is a blood vessel, and the device can be used to block blood flow. In some embodiments the device includes bioactive agents.

24 Claims, 8 Drawing Sheets

(56) References Cited

U.S. PATENT DOCUMENTS

| | | | |
|---|---|---|---|
| 5,102,417 | A | 4/1992 | Palmaz |
| 5,656,036 | A | 8/1997 | Palmaz |
| 5,925,063 | A | 7/1999 | Khosravi |
| 5,954,766 | A | 9/1999 | Zadno-Azizi et al. |
| 2003/0187474 | A1 | 10/2003 | Keegan et al. |
| 2003/0229366 | A1 | 12/2003 | Reggie et al. |
| 2004/0055606 | A1 | 3/2004 | Hendrickson et al. |
| 2006/0009798 | A1 | 1/2006 | Callister et al. |

OTHER PUBLICATIONS

Serbinenko, F. A., Occlusion by Ballooning of Sacular Aneurysms of the Cerebral Arteries, Vopr. Neirokhir, Jul.-Aug. 1974, pp. 8-15, vol. 4.

Serbinenko, F.A., Balloon Occlusion of a Cavernous Portion of the Carotid Artery as a Method of Treating Carotid-Cavity Anastomoses, Vopr. Neirokhir, Nov.-Dec. 1971, pp. 3-9, vol. 6.

Wehman, et al., Giant Cerebral Aneurysms: Endovascular Challenges, Neurosurgery, Nov. 2006, pp. S125-S138, vol. 59, No. 5.

Luo et al., Endovascular Treatment of the Carotid Artery Rupture with Massive Hemorrhage, J. Chin Med Assoc., Mar. 2003.

Hirai et al., Emergency Balloon Embolization or Carotid Artery Rupture Secondary to Postoperative Infection, Cardiovasc Intervent Radiol, 1996, pp. 50-52, vol. 19.

Berguer et al., Cure by Combination of Operation and Detachable Intravascular Balloon, Ann. Surg. Jul. 1982, pp. 65-68, vol. 196, No. 1.

Kaufman, et al., Detachable Balloon-modified Reducing Stent to Treat Hepatic Insufficiency after Transjugular Intrahepatic Portosystemic Shunt Creation, J Vasc Interv Radiol., May 2003, pp. 635-638, vol. 14, No. 5.

Tasar, et al., Intrahepatic arterioportal fistula and its treatment with detachable balloon and transcatheter embolization with coils and microspheres, Journal of Clinical Imaging, 2005, pp. 325-330, vol. 29.

White, et al., Occlusion of Varicoceles with Detachable Balloons, Radiology, May 1981, pp. 327-334, vol. 139.

Pollak et al., Clinical Results of Transvenous Systemic Embolotherapy with a Neuroradiologic Detachable Balloon, Radiology, May 1994, pp. 477-482, vol. 191, No. 2.

Makita, et al., Guide-Wire-directed Detachable Balloon: Clinical Application in Treatment of Varicoceles, Radiology, 1992, pp. 575-577, vol. 183.

Reidy et al., Transcatheter occlusion of a Blalock-Taussig shunt with a detachable balloon in a child, Bri Heart Journal, 1983, pp. 101-103, vol. 50.

DeSouza et al., Embolization with detachable Balloons—Applications outside the head, Clinical Radiology, Apr. 21, 1992, pp. 170-175, vol. 46.

Reidy et al., Transcatherer occlusion of coronary to bronchial anastomosis by detachable balloon combined with coronary angioplasty at same procedure, Brit Heart J. 1983, pp. 284-287, vol. 49.

Aydogan, Transcatheter Embolization Treatment of Coronary Arteriovenous Fistulas, Asian Cardiovascular & Thoracic Annals, 2003, pp. 63-67, vol. 11, No. 1.

Marshall et al., Treatment of Traumatic Renal Arteriovenous Fistulas by Detachable Silicone Balloon Embolization, The Journal of Urology, Aug. 1979, pp. 237-239, vol. 122.

Kadir et al., Therapeutic Embolization of the Kidney with Detachable Silicone Balloons, The Journal of Urology, Jan. 1983, pp. 11-13, vol. 129.

Hawkins et al., The Permeability of Detachable Latex Rubber Balloons—An In Vitro Study, Investigative Radiology, Dec. 1987, pp. 969-972, vol. 22.

Perala et al., Comparison of Early Deflation Rate of Detachable Latex and Silicone Balloons and Observations on Persistent Varicocele, J. Vasc. Interv. Radiol. Sep.-Oct. 1998, pp. 761-765, vol. 9, No. 5.

Cheng et al., Minimally Invasive Keyhole Approach for Removal of a Migratory Balloon Complicated by Endovascular Embolization of a Carotid-Cavernous Fistula, Minim. Invasive Neurosurgl, 2006, pp. 305-308, vol. 49.

Kallmes et al., The Use of Hydrocoil for Parent Artery Occlusion, AJNR Am J Neuroradiol, Sep. 2004, pp. 1409-1410, vol. 25.

Ferro et al., Percutaneous Transcatheter Embolization of a Large Pulmonary Arteriovenous Fistula with an Amplatzer Vascular Plug, Cardovacs Intervent Radiol, 2007, pp. 328-331, vol. 30.

Ross et al., The Vascular Plug: A New Device for Parent Artery Occlusion, AJNR Am J Neuroradiol, Feb. 2007, pp. 385-386, vol. 28.

METHODS AND APPARATUS FOR RAPID ENDOVASCULAR VESSEL OCCLUSION AND BLOOD FLOW INTERRUPTION

CROSS-REFERENCES TO RELATED APPLICATIONS

This application is a continuation application of U.S. patent application Ser. No. 11/825,956, now U.S. Pat. No. 8,328,840, entitled "Methods and Apparatus for Rapid Endovascular Vessel Occlusion and Blood Flow Interruption" and filed on Jul. 9, 2007, which is hereby incorporated by reference in its entirety for all purposes.

FIELD OF THE INVENTION

The invention is related to apparatus and methods for acutely occluding vessels in the body.

BACKGROUND OF THE INVENTION

Rapid, well-controlled, and safe methods to limit bleeding in vessels have encouraged the development of endovascular devices and techniques, and their introduction into clinical practice. Early devices used balloons, either non-detachable or later detachable, in order to block vessels, for example, in the treatment of carotid-cavernous fistulas and saccular aneurysms (Serbinenko, Neurosurg. 41: 125-145, 1974; Vopr. Neirokhir. July-August (4): 8-15. 1974; Vopr. Neirokhir. 35(6): 3-9, 1971).

Typically made from latex or silicone, balloons are delivered to a desired location in a vessel, then inflated in order to physically occlude the vessel. While other devices have since been developed, balloon occlusion remains in use, and is indicated for use in treating a variety of life-threatening conditions, including for example, giant cerebral and skull base aneurysms (Wehman et al., Neurosurg., 59: S125-S138, 2006), traumatic and non-traumatic vessel injury or rupture (Luo et al., J. Chin. Med. Assoc. 66: 140-147, 2003; Hirai et al., Cardiovasc. Intervent. Radiol. 19: 50-52, 1996), vertebro-vertebral arteriovenous fistulas (Berguer et al., Ann. Surg. 196: 65-68, 1982), and pre-operative tumor resections.

Detachable balloons are also useful clinically in procedures outside of neurological intervention. For example, balloons can be useful in flow reduction procedures such as shunt occlusion in patients with transjugular intrahepatic portosystemic shunts and hepatic insufficiency (Kaufman et al., J. Vas. Interv. Radiol. 14: 635-638, 2003), intrahepatic arterioportal fistulas (Tasar et al., Clin. Imag. 29: 325-330, 2005), treatment of varicoceles (White et al., Radiol. 139: 327-334, 1981; Pollak et al., Radiol. 191: 477-482, 1994; Makita et al., Radiol. 183: 575-577, 1992), shunt occlusion in patients with a Blalock-Taussig shunt (Reidy et al., Brit. Heart. J. 50: 101-103, 1983; DeSouza & Reidy, Clin. Radiol. 46: 170-175, 1992), obliteration of pulmonary arteriovenous fistulas, arteriovenous malformations or aortopulmonary anastomoses (Pollak et al., Radiol. 191: 477-482, 1994; DeSouza & Reidy, Clin. Radiol. 46: 170-175, 1992; Reidy et al., Brit. Heart J. 49: 284-287, 1983), coronary arteriovenous fistulas (Aydogan, Asian Cardiovasc. Thorac. Ann. 11: 63-67, 2003), or renal arteriovenous fistulas (Kadir et al., J. Urol. 129: 11-13, 1983; Marshall et al., J. Urol. 122: 237-239). Detachable balloons are also used in preoperative devascularization before surgical resection of organs such as the kidney (Kadir et al., J. Urol. 129: 11-13, 1983).

SUMMARY OF THE INVENTION

Despite their usefulness, balloon occlusion devices suffer from limitations that affect their ease of use and safety. By its very nature, a balloon can expand and rupture, or alternatively it can spontaneously deflate over time (Hawkins & Szaz, Invest. Radiol. 22: 969-972, 1987). Deflation is more common with latex balloons, with some studies reporting 100% deflation rates (Perala et al., J. Vasc. Interv. Radiol. 9: 761-765, 1998). Spontaneous deflation can result in treatment failure and reoccurrence of the lesion (Pollak et al., Radiol. 191: 477-482, 1994; Perala et al., J. Vasc. Interv. Radiol. 9: 761-765, 1998).

Detachable balloon devices present other problems as well, and their use in the intracranial vasculature presents specific challenges. For example, balloons lack trackability, meaning that they are difficult to navigate, especially through tortuous vessels, such as those commonly found in the intracranial circulation. In addition, premature (i.e., non-intentional) detachment from the delivery device can lead to adverse consequences such as cerebral artery blockage and stroke.

Even once in place they typically move forward during the process of inflation, making placement of the unexpanded balloon in order to achieve precise positioning after inflation relatively difficult. Balloons that dislodge and migrate can require open skull surgery especially where the balloon has become lodged in a major vessel, for example, in a cerebral artery (Cheng et al., Minim. Invasive Neurosurg., 49: 305-308, 2006).

More recently, detachable balloons have become unavailable for use in the United States. Further, silicone balloons were retired from the market several years ago, and the only alternative, the Goldvalve™ latex balloon, is difficult to obtain, and its use carries the risk of adverse reaction in patients allergic to latex. Thus, a vacuum exists in the field of vessel occlusion therapies, and consequently, interventionalists are left with few options to perform vessel occlusion procedures.

One approach has been to use hydrogel-coated coils in order to produce rapid vascular occlusion (Kallmes & Cloft, Am. J. Neuroradiol. 25: 1409-1410, 2004). However, there still remains a significant period of time between placement of the coil, and formation of the occlusive clot, even when using coated coils. This leads to concern that during formation of the clot, distal clot migration can occur, with potentially devastating consequences such as stroke. Further, the geometric configuration and unpredictability of coil-based embolization prevents precise occlusion of a short vascular segment. The risk of distal migration of a clot is also of concern when treating high-flow peripheral lesions such as pulmonary arteriovenous fistulas (Ferro et al., Cardiovasc. Intervent. Radiol. 30: 328-331, 2007).

The Amplatzer® Vascular Plug, a device made of a self-expanding Nitinol mesh, can be used to block flow through a vessel by inducing formation of a clot. However, as discussed above, this device is unable to provide for acute occlusion therapy and thus the risk of distal clot migration into remains. The device is also limited by it navigability, and placement precision, which limits its utility to use in performing occlusions below the base of the skull (Ross & Buciuc, Amer. J. Neurorad. 28(2): 385-286, 2007).

As a result of the limitations in prior art apparatus and methods for occluding vessels, the present disclosure recognizes that it is desirable to provide an apparatus and method that effectively provides acute blockage of a desired vessel, or alternatively, limited flow through a vessel, is relatively easy to place and deploy, and which will be stable over time, while avoiding limitations and problems inherent in the prior art apparatus and methods.

Accordingly, in some embodiments, there is provided a medical device for use in occluding a lumen of a body cavity, comprising: an expandable member having a lumen passing therethrough, the expandable member comprising first and second ends; the expandable member expandable from a first conformation to a second conformation; wherein, when the expandable member is in the second conformation, the device engages a surface of the body cavity; and a flow-limiting member coupled to the expandable member; wherein the flow-limiting member comprises a valve, positioned at the first end of the expandable member; the valve being movable between an open and a closed configuration; and wherein, when in the closed configuration and placed in the lumen of the body cavity, the valve substantially prevents a flow of a fluid in the lumen of the body cavity past the flow-limiting member.

In some embodiments, the device further comprises an expansion member, located within at least a portion of the lumen of the expandable member, effective to expand the expandable member from the first conformation to the second conformation. In some embodiments, the expansion member comprises a balloon, and the expandable member comprises a balloon-expandable stent.

In some embodiments, the device further comprises a delivery member coupled to the device and configured to pass through the valve. In some embodiments, the delivery member further comprises at least one catch member; wherein the at least one catch member is effective to engage the flow-limiting member at the valve; such that a force applied to the delivery member results in a substantial transfer of the force to the flow-limiting member via the at least one catch member.

In some embodiments, at least a portion of the flow-limiting member is invertible upon application of a sufficient force applied to the delivery member, when said force is substantially transferred to the flow-limiting member via the at least one catch member. In some embodiments, the catch member and flow-limiting member disengage upon application of a sufficient force applied to the delivery device, after the catch member and flow-limiting member have been engaged.

In some embodiments, the delivery member comprises a guide wire.

In some embodiments, the first end of the expandable member comprises a tapered portion.

In some embodiments, the flow-limiting member comprises a biocompatible polymer.

In some embodiments, at least one of the expandable member and the flow-limiting member further comprises at least one bioactive agent. In some embodiments, the at least one bioactive agent is effective to promote at least one healing of the body cavity, occlusion of the body cavity, retarding inflammation, and sealing of the device to an inner surface of the body cavity.

In some embodiments, the device comprises a plurality of flow limiting members, and at least one space between two of the plurality of the flow limiting members. In some embodiments, the device further comprises at least one bioactive agent located within the at least one space. In some embodiments, the at least one bioactive agent is effective to promote at least one healing of the body cavity, occlusion of the body cavity, retarding inflammation, and sealing of the device to an inner surface of the body cavity.

In some embodiments, the body cavity comprises a blood vessel. In some embodiments, at least one of the expandable member and the flow-limiting member further comprise at least one bioactive agent effective to promote formation of a thrombus.

In some embodiments, the expandable member is self-expanding. In some embodiments, the self-expanding member comprises a shape memory material.

In some embodiments, there is provided a method of occluding a lumen of a body cavity, comprising the steps of: providing a medical device, said device comprising: an expandable member having a lumen passing therethrough, the expandable member comprising first and second ends; the expandable member being expandable from a first conformation to a second conformation; wherein, when the expandable member is in the second conformation and is placed in the lumen of the body cavity, the device engages a surface of the body cavity; a flow-limiting member coupled to the expandable member; wherein the flow-limiting member comprises a valve, positioned at the first end of the expandable member; and the valve being movable between an open and a closed configuration, such that in the closed position, the valve substantially prevents a flow of a fluid through the lumen of the body cavity past the flow-limiting member; placing the device in the lumen of the body cavity; and expanding the expandable member from the first conformation to the second conformation.

In some embodiments, the method further comprises, moving the valve to a closed configuration, thereby substantially occluding the lumen of the body cavity.

In some embodiments, the expandable member is self-expanding, the device further comprises a sheath to maintain the device in the first conformation, and deploying the device further comprises removing the sheath, resulting in the expandable member expanding to the second conformation.

In some embodiments, the expandable member comprises a balloon-expandable stent, and deploying the device further comprises expanding a balloon located within at least a portion of the lumen of the device.

In some embodiments, the method further comprises providing a delivery member reversibly coupled to the device. In some embodiments, the delivery member further comprises at least one catch member, the at least one catch member effective to engage the flow-limiting member at the valve, and further comprising the step of: applying a sufficient force to the delivery member effective to result in substantial transfer of the force to the flow-limiting member via the at least one catch member.

In some embodiments, the method further comprises applying a sufficient force to the delivery member effective to result in inversion of at least a portion of the flow-limiting member, when said force is substantially transferred to the flow-limiting member via the at least one catch member.

In some embodiments, the method further comprises applying a force to the delivery member effective to disengage the at least one catch member from the flow-limiting member, after the at least one catch member and the flow-limiting member have been engaged. In some embodiments, the delivery member comprises a guide wire.

In some embodiments, the device further comprises at least one bioactive agent. In some embodiments, the at least one bioactive agent is effective to promote at least one of healing of the body cavity, occlusion of the body cavity, and sealing of the device to the surface of the body cavity. In some embodiments, the body cavity comprises a lumen of a blood vessel. In some embodiments, the at least one bioactive agent is effective promote thrombus formation.

In some embodiments, there is provide a device for occluding a lumen of a body cavity, comprising: means for engaging the body cavity from within the lumen; means for limiting flow, coupled to the means for engaging, effective to limit a flow of a fluid through the lumen and past the means for engaging; valve means, coupled to the means for limiting flow, and movable between an open position and a closed position; such that, in the closed position the valve means substantially prevents the flow of the fluid through the lumen and past the means for engaging.

BRIEF DESCRIPTION OF THE DRAWINGS

Embodiments of invention are best understood by reference to the accompanying figures, which are mean to illustrate, but not limit the invention.

DETAILED DESCRIPTION OF THE INVENTION

Figure 1:
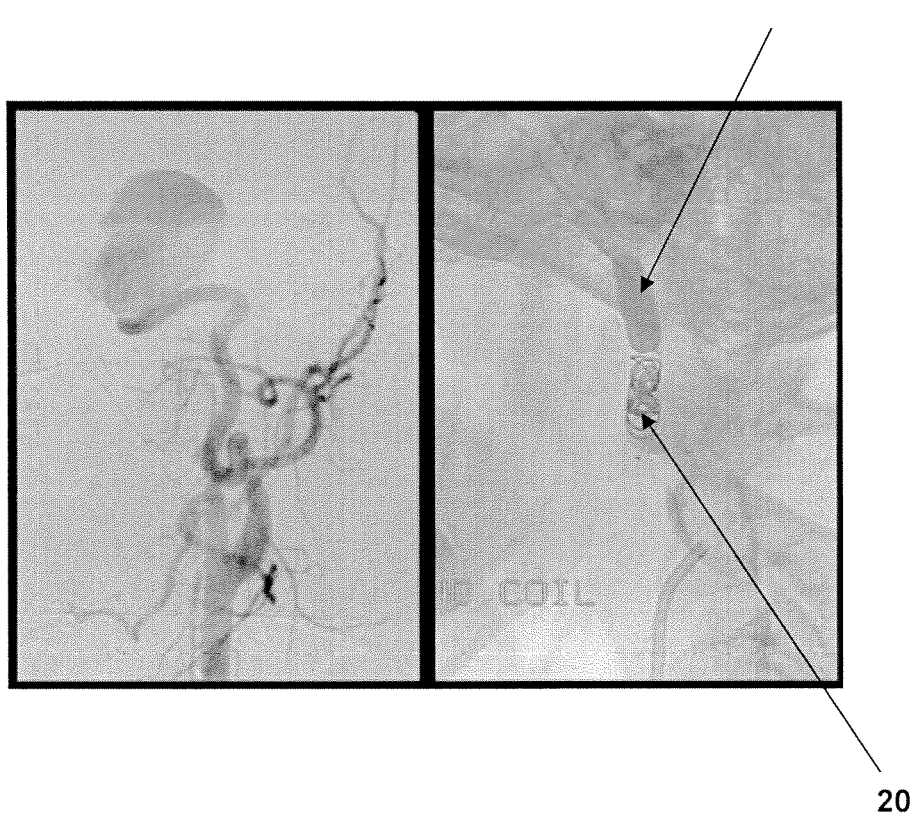
FIG. 1 is a radiograph showing the placement of a prior art balloon detachable stent and accompanying microcoil.

FIG. 1 is a radiograph illustrating a vessel occlusion using prior art methods and apparatus. The left panel of FIG. 1 shows a angiography image of a giant aneurysm prior to repair by balloon occlusion. The right panel is an image taken after the aneurysm had been occluded with the use of a prior art detachable balloon 10, which was further stabilized by the placement of microcoils 20. As discussed herein, these prior art methods suffer from a number of drawbacks and limitations that affect their general usefulness.

Figure 2:
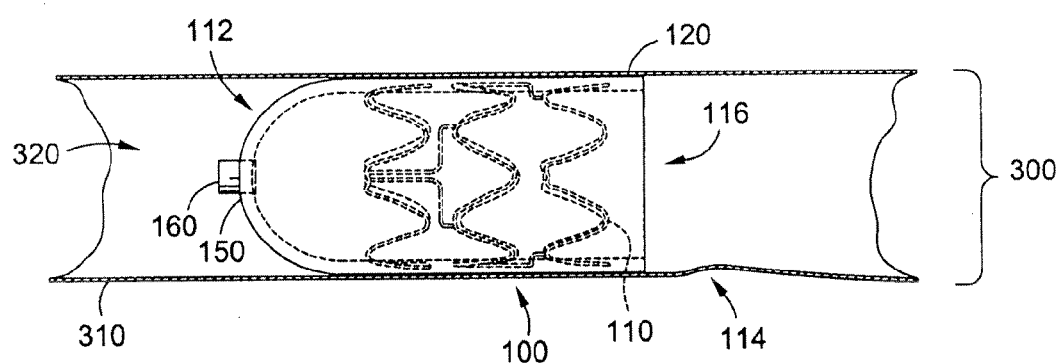
FIG. 2 is a side view of an embodiment of a vessel occluding device.

FIG. 2 illustrates an embodiment of a vessel occluding device 100 of the present disclosure. As used herein, the terms "occluding" and "occlusion" refer interchangeably to partial or completion blocking of the body cavity into which the device is deployed.

In some embodiments the device 100 comprises a scaffold structure formed by an expandable member 110. In some embodiments the expandable member 110 conveniently comprises an expandable stent. The expandable member comprises a distal end 112, a proximal end 114, and forms a generally tubular shape, with a lumen 116 within the scaffold structure. Stents are commonly used as supporting structure in cardiovascular and other vessel related procedures, for example, as a support as well as to maintain vessel patency after a balloon angioplasty procedure. The expandable member 110 can be self-expanding or balloon-expandable, or sized by any methods known to those of skill in the art.

Advantageously, a stent can be advanced within the lumen of a body cavity, for example, within a vessel, in a compressed or crimped conformation, Once in place the stent is either expanded or allowed to expand such that the device contacts a surface of the body cavity. In some embodiments the surface is an inner surface of the body cavity. In some embodiments, the body cavity is a vessel, for example, a blood vessel, and the device contact an inner surface of the vessel when deployed.

The expandable member 110 is adapted to serve as a framework for a flow-limiting member 120. In some embodiments the flow-limiting member 120 can be a cover located on the outer surfaces of the expandable member 110, in which case it will act as a cover to the scaffold. In some embodiments (not shown) the flow-limiting member 120 can be placed within the lumen 116 of the expandable member 110, analogous to an internal liner. In some embodiments a plurality of flow-limiting members can be used. For example, in some embodiments, two flow-limiting members can be used. Where two such members are used, a flow-limiting member can be placed both over and within the expandable member, both can be placed within the member, or both can be placed over the expandable member. In some embodiments, a plurality of flow-limiting members can be more than two. All such combinations and configurations are contemplated with be within the scope of the present disclosure. In some embodiments, there can be at least one space between two of the plurality of flow-limiting members, said at least one space useful to accommodate a bioactive agent or other substances useful to promote healing, occlusion, or attachment of the device to a surface of the body cavity engaged by the device.

In some embodiments, the flow-limiting member 120 encloses substantially the entire circumference of at least a portion of the length of the expandable member 110. In the pictured embodiments, the flow-limiting member 120 overlays the entire length of the expandable member 110. In some embodiments (not illustrated), the flow-limiting member 120 can cover less than the entire length of the expandable member 110. The cover also can substantially enclose the entire distal end of the expandable member 110. The expandable member 110 and flow-limiting member 120 act cooperatively, such that when the expandable member 110 is expanded within a vessel 300 to be occluded, the flow-limiting member 120 can be placed in intimate contact with an interior surface of a body cavity, for example, that of a vessel wall 310, such that the device 100 substantially fills the entire vessel lumen 320, effectively occluding flow through the vessel 300.

In some embodiments, a flow-limiting member 120 is situated on the outside of the expandable member portion, such that the cover contacts the inner surface of the body cavity to be occluded, for example, a blood vessel. In some embodiments, a flow-limiting member 120 can be located inside the expandable member portion, such that the expandable member portion contacts with the inner surface of the body cavity. In some embodiments, the scaffold is located within the matrix of the flow-limiting member, such that the flow-limiting member in effect provides a coating on the surface of the scaffold.

The flow-limiting member 120 can be made of any biocompatible polymer provided the material has certain mechanical properties that make it suitable for use in the device 100. Preferably, the material comprising the cover can be expanded by 800% or more of its unexpanded size without breaking. For example, the flow-limiting member 120 can be made of an elastomeric, or other highly compliant polymer. Such polymers include, but are not limited to, latex, styrene block copolymers, polyurethanes, polyolefins, polyester, polytetrafluoroethylene (PTFE), expanded polytetrafluoroethylene (ePTFE), polyethylene terephthalate (PET), and like materials well known to those skilled in the art. In some embodiments, the flow-limiting member 120 can comprise a stable swellable polymer that expands after a period of time in contact with a bodily fluid in order to improve the contact between the flow-limiting member 120 and the vessel wall 310.

The expandable member 110 can be fashioned from any suitable material, including, without limitation, stainless steel, platinum, tungsten, titanium, nickel or alloys thereof. In some embodiments the expandable member 110 can be made from a self-expanding material. In some embodiments, the expandable member 110 can be fashioned from a shape memory material, for example, Nitinol. Where a shape memory material is used, deployment can further involve subjecting the expandable member 110 to activation energy effective to cause the expandable member 110 to transform from the martensite to austentite arrangement, resulting in the stent transforming from the delivery to deployment configuration. In some embodiments the expandable member 110 and/or flow-limiting member 120 can be made from biodegradable materials should it be necessary to provide a device 100 that temporarily occludes a vessel, and then is later absorbed.

Figure 3A:
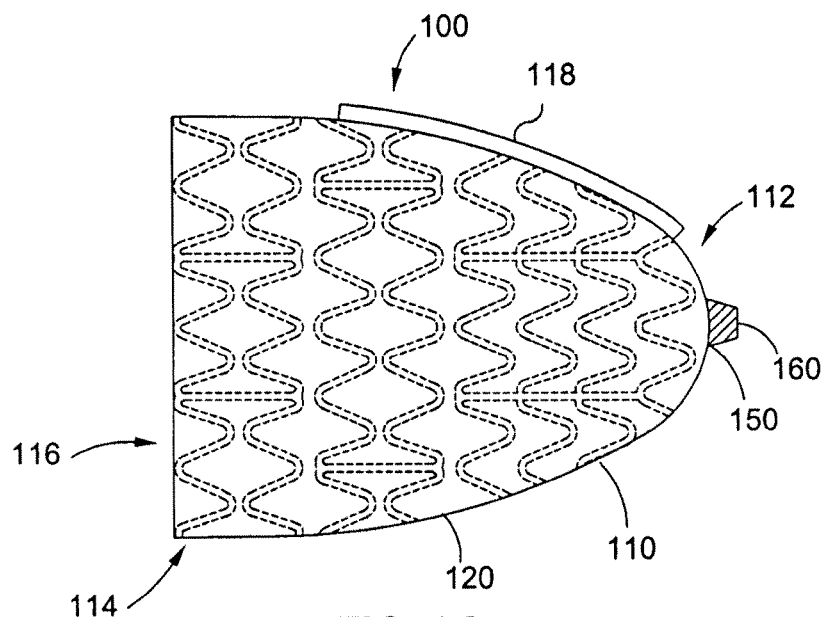
FIG. 3A is a side view of an embodiment of a tapered vessel occluding device.
Figure 3B:
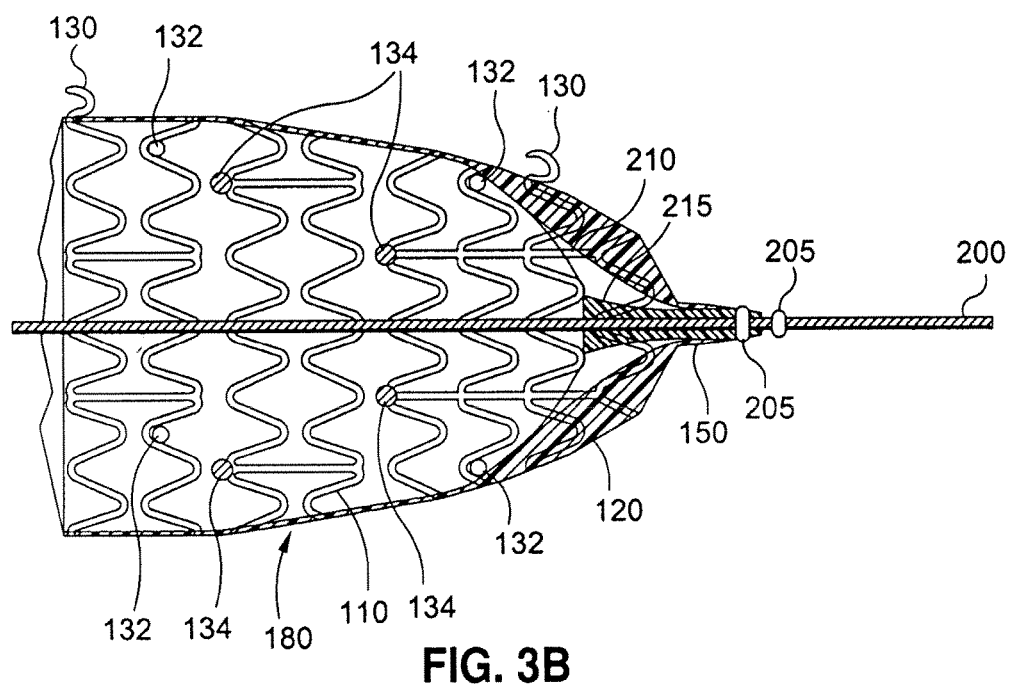
FIG. 3B is a side view of an embodiment of a tapered vessel occluding device, showing additional detail of the tip, the guide wire, and buildups on the guide wire that are used to invert the tip after delivery.

FIGS. 3A and 3B illustrate additional structural details of the device 100. For example, in some embodiments the stent comprises a tapered region 118. The tapered region 118 can provided additional support to the flow-limiting member 120. In addition, a stent with a tapered end provides improved trackability, making it easier to place the device in a desired location in a lumen of a body cavity, for example, in a vessel.

In some embodiments, the expandable member 110 may include barbs 130 or other like engagement structures, effective to further secure the device 100 to the vessel wall 310. Barbs 130 can be fashioned such that they protrude and engage the vessel wall when the device 100 is deployed. In some embodiments, barbs 130 can be fashioned from a shape memory material that is activated by an applied energy once the device 100 is in place, such that they "grasp" or otherwise engage the vessel wall. In some embodiments, the device can be secured with surgical sutures, such as where the device is deployed in a large caliber vessel. In these cases, suture holes 132 can be provided in the framework of the stent to permit easy attachment of the device to the vessel 100 using conventional surgical sutures.

The expandable member 110 can also include radioopaque markers 134 to improve radiographic visibility of the stent during deployment, as well as during post-surgical follow-ups. Markers 134 are well known in the art, and can be made, without limitation, of materials such as gold or platinum. The markers can be shaped and sized to permit the user to more easily orient the expandable member 110, thus allowing for more precise positioning of the device 100 in the vessel prior to deployment. Accurate positioning of the present device is one of the significant advantages the device disclosed herein provides over prior art detachable balloon devices, and the markers 134 improve positioning accuracy.

Also as shown in FIGS. 3A and 3B, in some embodiments, the flow-limiting member 120 further comprises a tip 150. In some embodiments, the tip 150 is contiguous with the remainder of the flow-limiting member 120. In some embodiments the tip 150 and flow-limiting member 120 can comprise separately manufactured pieces that are assembled prior to delivery and deployment of the device 100. The tip 150 and flow-limiting member 120 can comprise the same or different materials. The tip 150 can also be made to have a greater thickness than the remainder of the flow-limiting member 120 in order to improve resistance to flow, where the device 100 is deployed in a vessel with significant pressure, for example, in an artery. The area defined as the tip 150 can be variable in diameter. For example, the tip may be fractionally larger than a guide wire 200 used to deliver the device 100, or the tip can occupy essentially the entire distal end of the device 100, or the tip can be of any size in between these extremes.

As with other types of deployable stent devices, a guide wire 200 is conveniently used to move the device 100 into the desired location in the vessel 300, prior to final deployment. As the placement of a delivery member, such as a guide wire, necessitates the presence of a hole or other form of passageway in the flow-limiting member 120, the cover further comprises a valve 160, the valve 160 being effective to seal the distal end of the device following removal of the guide wire 200. Thus, on removal of the guide wire 200, the valve 160 is configured such that it assumes a closed conformation, blocking the hole through the guide wire 200 had been previously placed.

Figure 4:
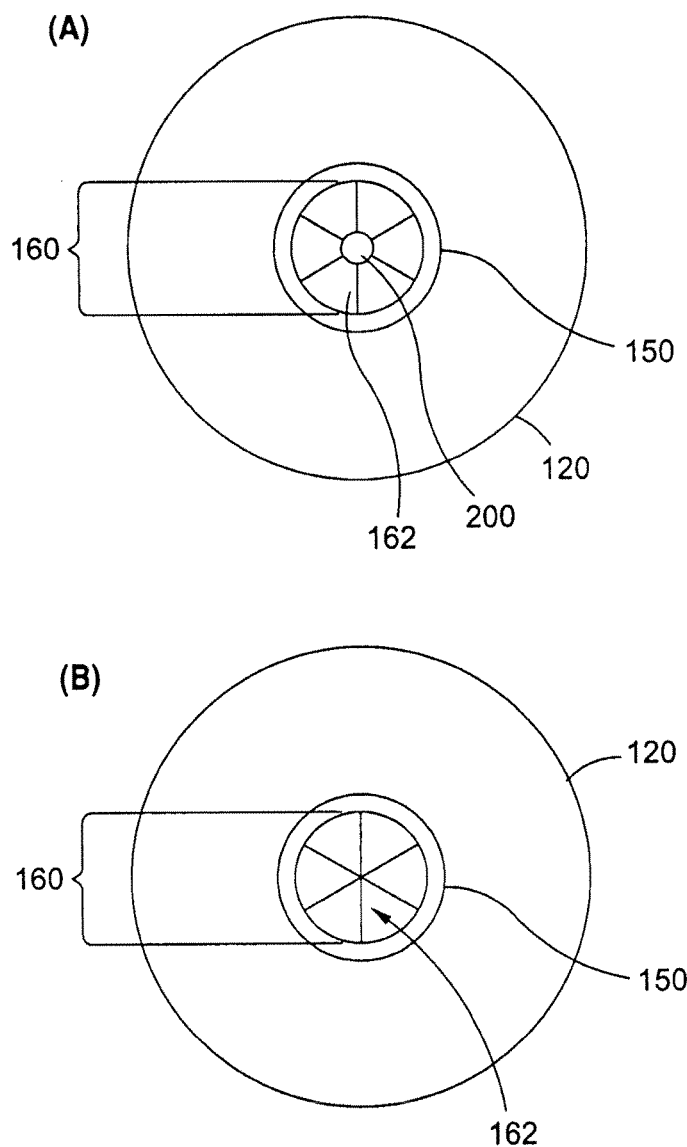
FIG. 4A is an end on view of the tip of the device, showing the arrangement of leaflets comprising the valve in the closed conformation.
FIG. 4B is an end on view of the tip of the device, showing the arrangement of leaflets comprising the valve when the device is mounted on a guide wire.

One embodiment of a valve is depicted in FIGS. 4A and 4B, where the tip 150, and valve 160, are shown in an end on view taken from the distal end of the device. In a some embodiments, a valve 160 comprises a plurality of valve leaflets 162. Preferably, the valve leaflets 162 are flexible and elastic, such that they can deform outwardly in a generally radial direction in order to accommodate the guide wire 200 (an open conformation), and then substantially snap-back on each other in a cooperative manner to close the hole after the guide wire 200 is removed (a closed conformation). In some embodiments the closed conformation is effective to seal the valve and prevent flow of material. In some embodiments, the closed conformation may result in the valve 160 providing an aperture, even in the absence of the guide wire 200 or other delivery member. In these cases, the device 100 will then function as a flow limiting device, thus permitting flow to be reduced to a reduced level (i.e., a partial occlusion of the vessel).

In addition to the illustrated embodiments, a variety of other "valve" structures are useful in conjunction with the present occluding device. Thus, any valve that effectively seals the distal end of the device when the delivery member, for example, the guide wire 200, is removed is considered to be within the definition of a valve as that term is used in the present disclosure. For example, where a valve comprising leaflets is used, the number of leaflets is not considered an essential feature of the valve. Thus valves with any number of leaflets can conceivably be used successfully. In some embodiments, a single flap, analogous to a reed valve, one type of which is disclosed in U.S. Pat. No. 4,089,348 to Yoshida et al. could comprise an effective valve.

Figure 5:
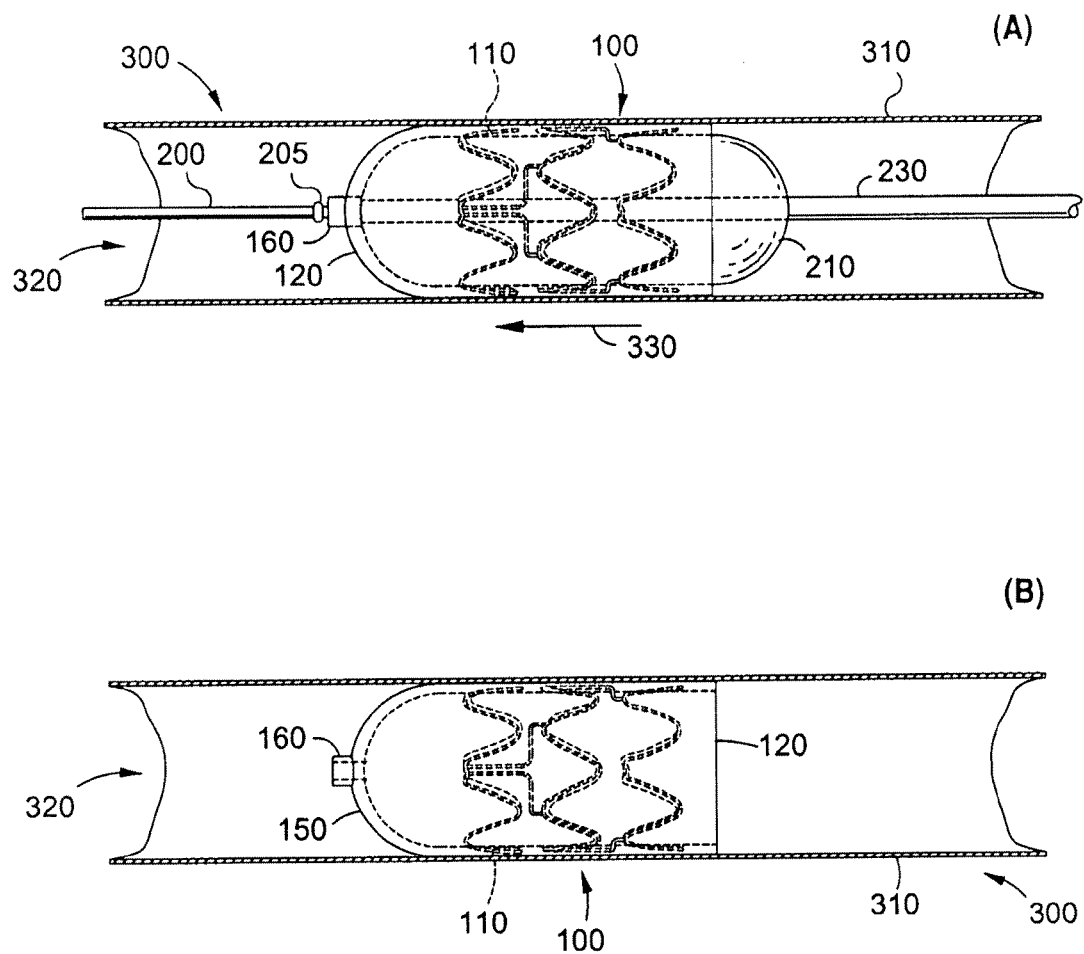
FIG. 5A shows a side view of a vessel occluding device placed in a "forward" direction, prior to final deployment, with components of the delivery system still attached.
FIG. 5B shows a side view of a vessel occluding device deployed in the "forward" direction.

The can be deployed in various configurations, as shown in FIGS. 5A, 5B, 6A, and 6B. In FIGS. 5A and 5B, the device is deployed in what is termed a "forward configuration," such that the distal end of the device 100 is oriented in the vessel 300 in the same direction as the direction of flow 330. In one embodiment, shown in FIG. 5A, the device is a balloon expandable device, and the system comprises the device, a delivery catheter 230, a guide wire 200, and a balloon 210, that expands the device so that it effectively fills the vessel lumen 320.

Figure 6:
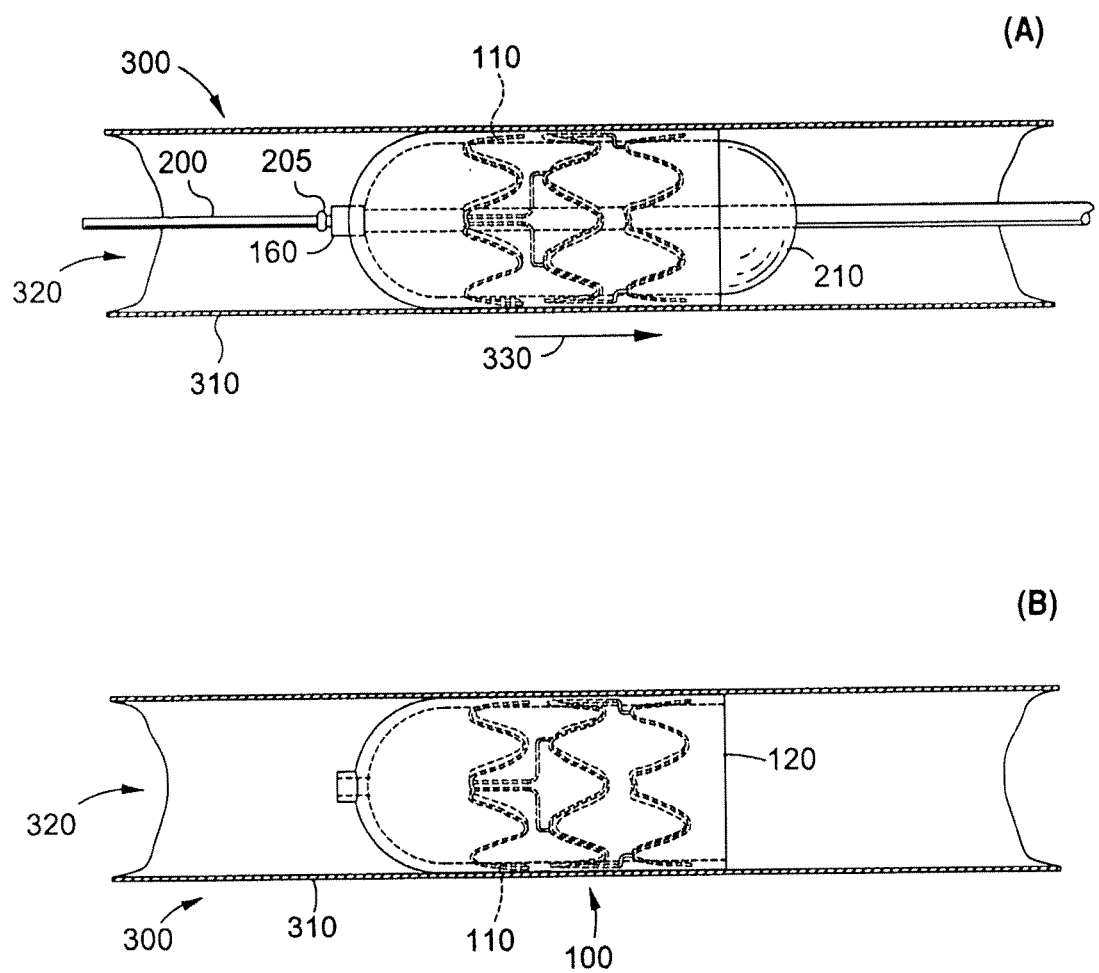
FIG. 6A shows a side view of vessel occluding device placed in a "reverse" direction prior to final deployment, with components of the delivery system still attached.
FIG. 6B shows a side view of a vessel occluding device deployed in the "reverse" direction.

In some embodiments, as shown in FIGS. 6A and 6B, the device 100 can be deployed in a "reverse" orientation, such that the distal end 112 of the device is pointed in a direction opposite (i.e., towards) the direction of flow 330 in the vessel 300.

In either forward or reverse deployment, the device 100 is advanced to the desired location by the use of a delivery system, for example, a delivery catheter and guide wire, as with conventional stent devices. The guide wire 200 is used to advance the device 100 along the length of the vessel to be occluded, and to place the device in the desired location. As discussed above, the device 100 can be tracked radiographically by visualizing radio-opaque markers included in the device structure.

In some cases the system will include an expandable member, such as an inflatable balloon which is used to expand the expandable member 110 and flow-limiting member 120 to fit up against a vessel wall 310. In some embodiments the system can comprises a sheath to encase and maintain the device 100 in a compressed state, such as where a self-expanding stent is used in the device 100. For example, a stent delivery catheter and sheath such as that disclosed in U.S. Pat. No. 6,120,522 to Vrba et al. is one possible system for safely delivering a device 100 comprising a self-expanding stent.

Figure 7A:
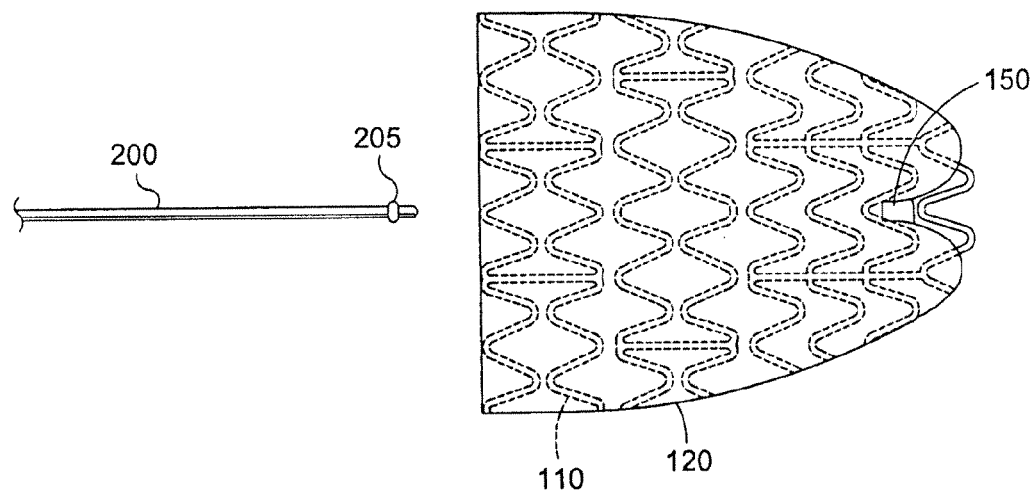
FIG. 7A is a detailed side view of an embodiment of a vessel occluding device, showing the tip in an inverted position as would be the case following deployment.
Figure 7B:
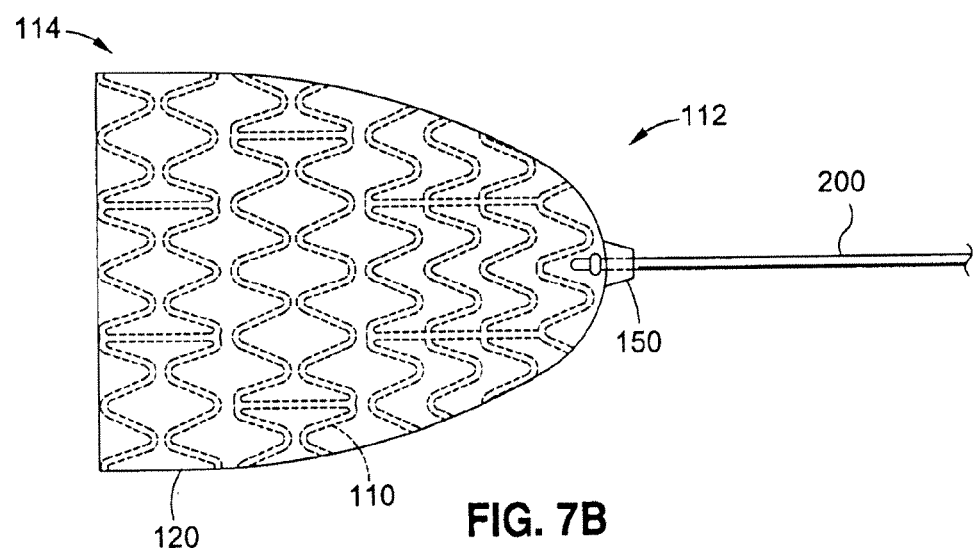
FIG. 7B is a side view of an embodiment of a vessel occluding device in which the guide wire is mounted from the distal end of the device.

In some embodiments, the delivery member (e.g., a guide wire) is inserted into the tip 150 from the proximal end 114 via the device lumen 116 as shown in the illustrations. In some embodiments, the delivery member can alternatively be inserted into the tip 150 from the distal end 112 of the device 100, as shown in FIG. 7B. Deploying the device using an arrangement as shown in FIG. 7B can provide an advantage when deploying in tapered vessels.

After placement of the device 100, the expandable member 110 is expanded (or allowed to expand) such that the expandable member 110 forces the flow-limiting member 120 up against the inner surface of the vessel 300. At this point, the device 100 can be further secured by the use of sutures, or by engaging the vessel wall 310 with barbs 130 or other similar engagement structures. Once the device is secured in place, the guide wire 200 can be removed by pulling on the proximal end in order to withdraw the wire from the device, as shown in FIG. 7A.

Returning to FIG. 3B (also shown in FIGS. 5A and 6A), the guide wire 200 and optionally the tip 150, can further comprise at least one catch member 205. The catch member 205 is configured such that as force is applied to the proximal end of the guide wire to pull it from the device 100, the catch member will engage the tip 150. With continued application of force to withdraw the guide wire 200, the force will be transmitted by the catch members 205 to the tip 150, such that the tip will be pulled inwardly in a proximal direction. With continued pulling on the guide wire, the tip 150 will become inverted into the device lumen 116.

Conveniently, the catch members 205 and the valve 160 are configured such that sufficient force can be applied to the tip in order to result in its inversion into the lumen 116, but with addition force, the valve 160 will yield such that the guide wire 200 can be uncoupled from the device 100 and completely removed from the patient. An example of the device after inversion of the tip 150 and withdrawal of the guide wire 200 is provided in FIG. 7A.

Inversion of the tip improves the sealing function of the valve, especially when the device is deployed in the "forward" configuration, and the valve embodies a leaflet type of structure. Inversion of the tip 150 will tend to produce a bias force that will cause the leaflets to be forced more tightly together, improving the engagement of the leaflets, and the sealing of the distal end of the device 100 by the valve 160 and cover 120. In addition, pressure within the body cavity will cooperate with the valve structure to further compress the valve. This will in turn promote more effective sealing of the valve further enhancing the sealing function of the valved portion of the device.

In some embodiments the material in the valve 160, can comprise a material that swells in response to contact with the contents of the vessel lumen. For example, the material can swell after contact with blood in a blood vessel, and can further include micro-pockets that trap substances present in the vessel lumen 320. Again, this feature will improve sealing.

While a common objective will be to completely occlude a vessel, in some cases it can be desirable to provide a device that operates as a flow restrictor, rather than a complete barrier. In these cases rather than a valve per se, the tip 150 may comprise a hole in place of the valve. The hole would be effective to permit a reduced flow through the vessel.

As indicated above, in some embodiments the flow-limiting member 120 is manufactured as a single piece. The portion of the flow-limiting member 120 contacting the expandable member 110 is preferably relatively thin in order to accommodate the range of extension that is expected to be encountered as the stent is expanded from the delivery size to the deployed size. As a result, the flow-limiting member 120 should be able to accommodate stretching to 800% or more, relative to its unexpended size. The tip 150, which does not need to be as extensible, can be of increasing thickness towards the longitudinal axis of the device in order to provide increased strength.

Figure 8:
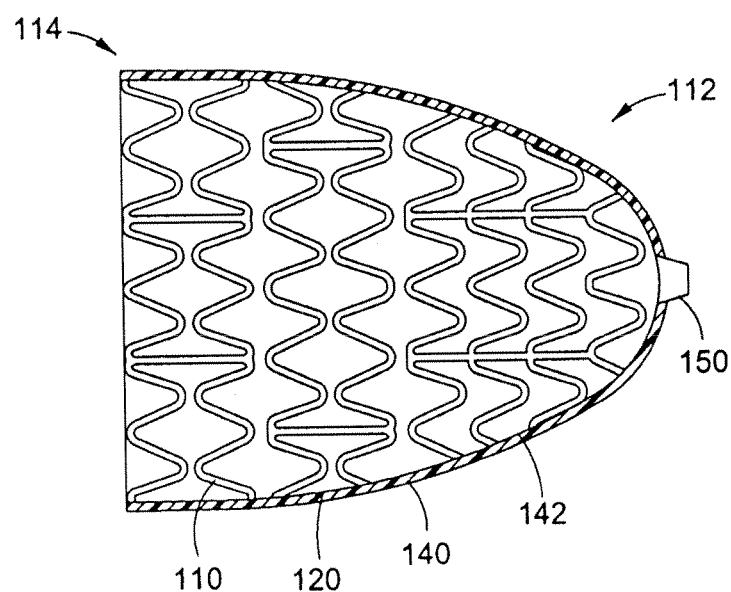
FIG. 8 is a side view of an embodiment of a vessel occluding device in which the device comprises a cover with two layers, and space between the layers for inclusion of a bioactive substance.

In some embodiments the flow-limiting member 120 can comprise more than one layer, as shown in FIG. 8. For example, it may be desirable to provide a second layer 140, in addition to the first flow-limiting member 120, and a space 142 between the flow-limiting member 120 and second layer 140 into which can be placed pharmacologic agents or other bioactive agents. In some embodiments, the second layer 140 operates as another flow-limiting member. The bioactive agent or other agents can be effective to aid in sealing the device to the vessel wall, or to promote formation of a localized thrombus, as in the case where the vessel to be occluded is a blood vessel, or to promote occlusion of the lumen of the body cavity generally. As described above, where a plurality of flow-limiting members are provided, a number of possible arrangements are possible, and are intended to be included with the scope of the present disclosure. For example, the flow-limiting member and second layer can both be placed over the expandable member, both can be placed within the lumen of the expandable member, or one can be placed over the expandable member and the other placed within the lumen. Thus, all such combinations and configurations of flow-limiting member, expandable member, and second, or even third or greater numbers of layers of are within the scope of the present disclosure.

In embodiments of the device with an second layer 140, the second layer 140 can also comprise biodegradable polymers or coatings, or can be permeable and biostable, or a combination of degradable and stable polymers. For example, U.S. Pat. No. 5,707,385 to Williams, discloses an expandable sheath that incorporates a therapeutic drug that can be delivered in a sustained release fashion from a reservoir situated between two adjacent layers of the sheath. Likewise, U.S. Pat. No. 7,041,130 to Santini, Jr. et al., discloses a device for the controlled release of drugs comprising an implantable stent and therapeutic agents in a biodegradable matrix.

Thus, some embodiments of the present device can include a cover having one or more layers, of which at least one is capable of releasing a therapeutic agent in a controlled or sustained release fashion. Therapeutic agents can include, without limitation, blood clotting factors I, Ia, II, IIa, V, Va, VII, VIIa, VIII, VIIIa, IX, IXa, X, Xa, XII, XIIa, XIII, XIIIa, zeolites, desmopressin, tranexamic acid, aminocaproic acid, and aprotinin Additional agents can include factors that promote healing in case of vessel injury when placing the device. These can include growth factors, cytokines, and other agents that would be expected to promote healing and/or endothelialization.

The flow-limiting member 120 can also include permanently attached agents that promote the binding of factors, or the recruitment of specific cell types to the cover material, as can the expandable member, or the second layer 140.

The device of the present disclosure, and its use, provides a number of advantages when compared to prior art devices and methods. For example, the process of preparing detachable balloons typically involves a complex process of removing all the air from the balloon, and then attaching the balloon to the delivery catheter.

In contrast, some embodiments of the present device are conveniently mounted onto a conventional expandable balloon delivery system as used with other types of balloon-expandable stents. In some embodiments, therefore, the a system is provided that includes the device 100, a balloon 98, and a delivery catheter.

In some embodiments, the stent of the present disclosure can be a self-expanding stent, loaded inside a delivery sheath, and then delivered to the desired vessel, again by conventional devices and methods well known in the art.

The device as disclosed herein is also easier to place and deploy than prior art devices, in particular detachable balloons. When using detachable balloons it is common to either push the balloon off the delivery catheter, or to inflate and pull the catheter off the balloon (Hieshima, et al., *Radiol.* 138: 227-228, 1981). In either case, poor tracking of the balloon, or migration of the balloon after detachment are serious problems that can occur. As discussed above, the use of additional "safety" balloons, and/or microcoils, as stabilizers of the main occluding device, are solutions that have typically been resorted to (Masaryk et al., *Am. J. Neuroradiol.* 20: 1103-1106, 1999).

In contrast, embodiments of the present device are designed to be deliverable using standard rapid exchange or over-the-wire techniques commonly used with other types of stents. These delivery systems offer optimal trackability, an especially important feature when attempting to navigate certain vessels, such as those of the intracranial vasculature.

Delivery by guide wire provides additional advantages. For example, upon deployment, detachable balloons can and do migrate within the vessel as they are inflated. This creates the potential for mispositioning of the balloon. In contrast, embodiments as disclosed are precisely located by means of the guide wire, which is only removed once the device 100 is fully deployed at the desired location. The inclusion of radio-opaque markers 134 on the device, as described above, further improves the ability of the surgeon to precisely deploy the device 100. Further securement means, such as barbs 130, or suture holes 132, can be employed to better anchor the device at a desired location.

A significant problem encountered in the use of occlusion balloons is that they frequently spontaneously deflate, allowing for vessel recanalization, or even worse, migration of the balloon within the vessel. To deal with this problem, it has become customary to deploy more than one balloon, or to augment the embolization process with microcoils. Each of these solutions creates additional risk, as well as increasing the complexity of the procedure.

In contrast, embodiments of the present device do not present a risk of deflation. Both expandable and self-expanding stents are well known for long-term stability in patients. Stents provide the further advantage in that they do not deflate, and assuming they are manufactured from appropriate materials, will retain their deployed shape essentially indefinitely. As a result, occlusion using the present device as disclosed is effectively achieved using a single device, and the need for duplicate devices or other stabilizing structures such as microcoils is obviated. This reduces the time and complexity of the surgical procedures, and results in increased safety to the patient. In addition, as occlusion can be effectively achieved with a single device, shorter segments of vessel can be occluded than would be practically possible using prior art methods and devices. Vessels are also occluded essentially immediately upon deployment, and thus the risk of clot migration during the early stages of clot formation is avoided.

It is contemplated that, without being limiting, devices as disclosed would be effective in occluding vessels with luminal diameters ranging from about 2 mm to about 20 mm or even larger. In addition, the device 100 is not necessarily limited to use in the cardiovascular system, but may be useful in any body vessel where it is medically indicated to occlude flow through that vessel or tubular structure. Thus, the device 100 can be effectively deployed in the cardiovascular, respiratory, urinary, lymphatic, or reproductive systems.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A medical device for use in occluding a lumen of a body cavity, comprising:
　an expandable member having a lumen passing therethrough;
　the expandable member being expandable from a first conformation to a second conformation;
　wherein the device is configured to engage a surface of the body cavity when the expandable member is in the second conformation; and
　a flow-limiting member with first and second end portions opposite one another, the flow-limiting member being coupled to the expandable member;
　wherein the flow-limiting member comprises a valve positioned at a first end section of the expandable member;
　wherein the valve is movable between an open and a closed configuration;
　wherein the valve comprises a first leaflet and a second leaflet that are movable between the open configuration and the closed configuration, and when the first leaflet and the second leaflet are in the closed configuration, the first leaflet is in contact with the second leaflet;
　wherein the flow-limiting member is configured such that when a force directed proximally is exerted on the first end portion, the first end portion inverts from a non-inverted configuration to an inverted configuration such that the first end portion moves toward the second end portion and such that a bias force increases a contact pressure between the first leaflet and the second leaflet; wherein, when in the closed configuration and placed in the lumen of the body cavity, the valve substantially prevents a flow of a fluid in the lumen of the body cavity past the flow-limiting member;

wherein, after the first portion inverts from the non-inverted configuration to the inverted configuration, the first and second leaflets each remain substantially at a same angle, relative to a direction of the inverting, as before the inverting; and wherein the first leaflet extends, from a non-free end of the first leaflet to a free end of the first leaflet, in substantially the same direction before and after the inverting.

2. The medical device of claim 1, wherein the expandable member comprises (a) an inner surface defining the lumen through the expandable member and (b) an outer surface.

3. The medical device of claim 2, wherein the outer surface is configured to engage the surface of the body cavity when the expandable member is in the second conformation.

4. The medical device of claim 2, wherein the flow-limiting member resides within the lumen.

5. The medical device of claim 1, wherein, when the first end portion is inverted, a distalmost surface of the flow-limiting member lies proximal to a distalmost surface of the expandable member.

6. The medical device of claim 1, wherein the expandable member comprises multiple protuberances at a distal portion that extend more distally than the distalmost surface of the flow-limiting member when the first end portion is inverted.

7. The medical device of claim 1, wherein, when the first portion inverts from the non-inverted configuration to the inverted configuration, the first and second leaflets remain substantially perpendicular to the direction of the inverting.

8. The medical device of claim 1, wherein, when the first end portion is in the non-inverted configuration, free ends of the first and second leaflets are in the same position relative to one another as when the first end portion is in the inverted configuration.

9. The medical device of claim 1, comprising:
 a plurality of flow limiting members having at least one space between two of the plurality of the flow limiting members; and
 at least one bioactive agent located within the at least one space.

10. The medical device of claim 1, wherein, when the first portion inverts from the non-inverted configuration to the inverted configuration, the first and second leaflets remain substantially at a same angle relative to the direction of the inverting.

11. The medical device of claim 1, wherein the valve comprises a base member, wherein the non-free end of the first leaflet is attached to the base member, and wherein the non-free end of the first leaflet is opposite the free end of the first leaflet.

12. The medical device of claim 11, wherein the free end of the first leaflet is a tip of the first leaflet, and wherein the base member comprises a neck of the valve at which the non-free end of the first leaflet is attached.

13. The medical device of claim 1, wherein the second leaflet extends, from a non-free end of the second leaflet to a free end of the second leaflet, in substantially the same direction before and after the inverting.

14. A method of occluding a lumen of a body cavity, comprising the steps of:
 providing a medical device, said device comprising:
 an expandable member having a lumen passing therethrough;
 the expandable member being expandable from a first conformation to a second conformation;
 wherein, when the expandable member is in the second conformation, the device engages a surface of the body cavity; and
 a flow-limiting member with first and second end portions opposite one another, the flow-limiting member being coupled to the expandable member;
 wherein the flow-limiting member comprises a valve positioned at a first end section of the expandable member;
 wherein the valve is movable between an open and a closed configuration, such that in the closed configuration, the valve substantially prevents a flow of a fluid through the lumen of the body cavity past the flow-limiting member;
 wherein the valve comprises a first leaflet and a second leaflet that are movable between the open configuration and the closed configuration, and when the first leaflet and the second leaflet are in the closed configuration, the first leaflet is in contact with the second leaflet;
 placing the device in the lumen of the body cavity;
 expanding the expandable member from the first conformation to the second conformation; and
 inverting the first end portion from a non-inverted configuration to an inverted configuration such that the first end portion moves toward the second end portion and such that a bias force increases a contact pressure between the first leaflet and the second leaflet, when a force directed proximally is exerted on the first end portion; wherein, after the first portion inverts from the non-inverted configuration to the inverted configuration, the first and second leaflets each remain substantially at a same angle, relative to a direction of the inverting, as before the inverting, and
 wherein the first leaflet extends, from a non-free end of the first leaflet to a free end of the first leaflet, in substantially the same direction before and after the inverting.

15. The method of claim 14, wherein the expandable member comprises multiple protuberances at a distal portion that extend more distally than the distalmost surface of the flow-limiting member when the first end portion is inverted.

16. The method of claim 14, wherein, when the first end portion is in the non-inverted configuration, free ends of the first and second leaflets are in the same position relative to one another as when the first end portion is in the inverted configuration.

17. The method of claim 14, wherein, when the first portion inverts from the non-inverted configuration to the inverted configuration, the first and second leaflets remain substantially perpendicular to a direction of the inverting.

18. The method of claim 14, further comprising providing a delivery member reversibly coupled to the device.

19. The method of claim 18, wherein the delivery member further comprises at least one catch member, the at least one catch member effective to engage the flow-limiting member at the valve, and further comprising the step of:
 applying a sufficient force to the delivery member effective to result in substantial transfer of the force to the flow-limiting member via the at least one catch member.

20. The method of claim 19, further comprising:
 applying a force to the delivery member effective to disengage the at least one catch member from the flow-limiting member, after the at least one catch member and the flow-limiting member have been engaged.

21. A device for occluding a lumen of a body cavity, comprising:
- means for engaging the body cavity from within the lumen of the body cavity, the means for engaging having (a) an inner surface defining a lumen through the means for engaging and (b) an outer surface configured to engage a surface of the body cavity;
- means for limiting flow, coupled to the means for engaging, effective to limit a flow of a fluid through the lumen and past the means for engaging and comprising first and second end portions opposite one another, the means for limiting flow residing within the lumen of the means for engaging;
- valve means, coupled to the means for limiting flow, and movable between an open position and a closed position such that, in the closed position the valve means substantially prevents the flow of the fluid through the lumen and past the means for engaging;
- wherein the valve means comprises a first leaflet and a second leaflet that are movable between the open position and the closed position, and when the first leaflet and the second leaflet are in the closed position, the first leaflet contacts the second leaflet;
- wherein the means for limiting flow is configured such that when a force directed proximally is exerted on the first end portion, the first end portion inverts from a non-inverted configuration to an inverted configuration such that the first end portion moves toward the second end portion and such that a bias force increases a contact pressure between the first leaflet and the second leaflet;
- wherein, after the first portion inverts from the non-inverted configuration to the inverted configuration, the first and second leaflets each remain substantially at a same angle, relative to a direction of the inverting, as before the inverting, and
- wherein the first leaflet extends, from a non-free end of the first leaflet to a free end of the first leaflet, in substantially the same direction before and after the inverting.

22. The device of claim 21, wherein the means for engaging comprises multiple protuberances at a distal portion that extend more distally than the distalmost surface of the means for limiting flow when the first end portion is inverted.

23. The device of claim 21, wherein, when the first end portion is in the non-inverted configuration, free ends of the first and second leaflets are in the same position relative to one another as when the first end portion is in the inverted configuration.

24. The device of claim 21, wherein, when the first portion inverts from the non-inverted configuration to the inverted configuration, the first and second leaflets remain substantially perpendicular to a direction of the inverting.

* * * * *